United States Patent
Midlang et al.

(10) Patent No.: US 10,745,986 B2
(45) Date of Patent: Aug. 18, 2020

(54) REAL TIME MUD MONITORING

(71) Applicant: INTELLIGENT MUD SOLUTIONS AS, Hafrsfjord (NO)

(72) Inventors: Eivind Midlang, Vlk I Sogn (NO); George Gibbs Smith, Hafrsfjord (NO)

(73) Assignee: INTELLIGENT MUD SOLUTIONS AS, Hafrsfjord (NO)

( * ) Notice: Subject to any disclaimer, the term of this patent is extended or adjusted under 35 U.S.C. 154(b) by 0 days.

(21) Appl. No.: 16/512,073

(22) Filed: Jul. 15, 2019

(65) Prior Publication Data

US 2019/0345784 A1    Nov. 14, 2019

Related U.S. Application Data

(63) Continuation of application No. 14/911,596, filed as application No. PCT/NO2014/000038 on Aug. 13, 2014, now Pat. No. 10,385,636.

(30) Foreign Application Priority Data

Aug. 13, 2013 (NO) .................................. 20131105

(51) Int. Cl.
| | | |
|---|---|---|
| *E21B 21/08* | (2006.01) | |
| *E21B 21/01* | (2006.01) | |
| *G01N 33/28* | (2006.01) | |

(52) U.S. Cl.
CPC .............. *E21B 21/08* (2013.01); *E21B 21/01* (2013.01); *G01N 33/2823* (2013.01)

(58) Field of Classification Search
CPC ...... E21B 21/08; E21B 21/01; G01N 33/2823
See application file for complete search history.

(56) References Cited

U.S. PATENT DOCUMENTS

| | | |
|---|---|---|
| 3,610,026 A | 10/1971 | Topham |
| 4,557,142 A | 12/1985 | Hensley et al. |
| 6,378,628 B1 | 4/2002 | McGuire et al. |
| 8,121,971 B2 | 2/2012 | Edwards et al. |
| 8,575,541 B1 | 11/2013 | Jamison et al. |

(Continued)

FOREIGN PATENT DOCUMENTS

| | | |
|---|---|---|
| CA | 2005195 A1 | 6/1990 |
| CA | 2856743 A1 | 8/2013 |

(Continued)

OTHER PUBLICATIONS

Soufi, Naser, "International Search Report," prepared for PCT/NO2014/000038, dated Nov. 7, 2014, three pages.

(Continued)

*Primary Examiner* — Yasser A Abdelaziez
(74) *Attorney, Agent, or Firm* — Ross T. Robinson

(57) ABSTRACT

The invention provides a system for real time mud monitoring. The system is distinctive in that it comprises means for real time continuous or frequent measurement of a diversity of mud parameters of the mud being pumped into the well, said parameters at least comprising mud weight/density and viscosity, a skid where the means for measurements are arranged, said means are connected in real time to a mud process for measurements and to a data collection and analysis system connected in real time and interfaced to a mud engineer. Related method and use.

8 Claims, 1 Drawing Sheet

(56) References Cited

U.S. PATENT DOCUMENTS

| | | | |
|---|---|---|---|
| 2004/0149431 A1 | 8/2004 | Wylie et al. | |
| 2011/0125333 A1 | 5/2011 | Gray | |
| 2014/0291023 A1* | 10/2014 | Edbury | E21B 21/08 |
| | | | 175/24 |
| 2015/0083492 A1* | 3/2015 | Wassell | E21B 44/00 |
| | | | 175/24 |
| 2017/0239840 A1* | 8/2017 | Adams | B28B 19/0038 |

FOREIGN PATENT DOCUMENTS

| | | |
|---|---|---|
| CN | 201802388 U | 4/2011 |
| CN | 201804242 | 4/2011 |
| GB | 2445209 A | 7/2008 |
| MX | 2011006044 A | 7/2011 |
| WO | WO-0250398 A1 | 6/2002 |
| WO | WO-2007005822 A2 | 1/2007 |
| WO | WO-2007005822 A3 | 8/2007 |
| WO | WO-2011095600 A2 | 8/2011 |
| WO | WO-2011095600 A3 | 12/2011 |
| WO | WO-2012016045 A1 | 2/2012 |

OTHER PUBLICATIONS

Bloys, Ben, et al., "Designing and managing drilled fluid", Oilfield Review, vol. 6, No. 2, Apr. 30, 1990, pp. 33-43.

Integrated Sensing Systems, Inc. (ISSYS); White paper on Gas Density Meter; "MassSense Gas Density Meter—Advancing gas density measurement to a new level of performance, size and value!"; 2013; 2 pages.

Frank, A.; "Understanding Rheology of Structured Fluids"; TA Instrument Applicant Notes Library; Jan. 2004; 11 pages.

* cited by examiner

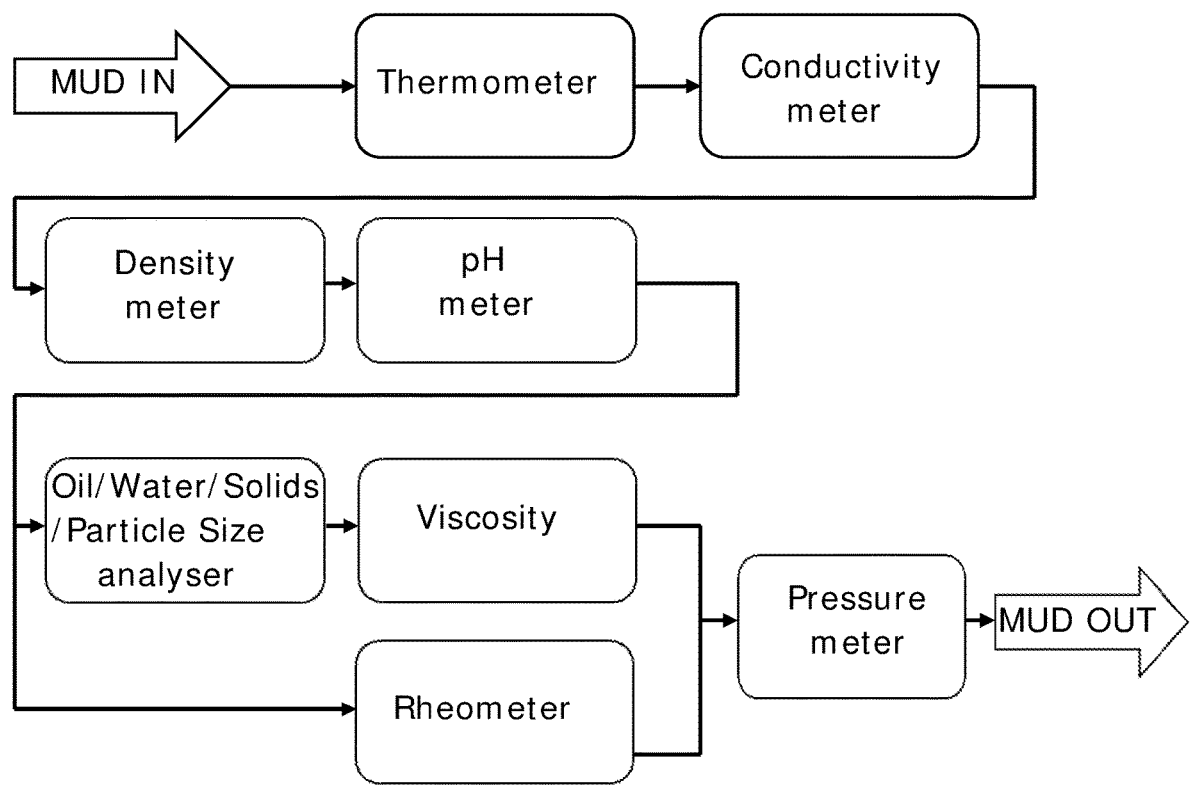

REAL TIME MUD MONITORING

FIELD OF THE INVENTION

The present invention relates to drilling of wells for exploration or production of petroleum fluids. More specifically, the invention relates to monitoring of the properties of the mud to be pumped into the well for pressure control and lubrication, monitoring of the properties of the mud returning from the well and using one or both of said mud properties as input for determining future adjustments of the properties of the mud to be pumped into the well.

BACKGROUND OF THE INVENTION AND PRIOR ART

Drilling of wells for exploration or production of petroleum fluids like oil, condensate and gas is very expensive, particularly offshore where the day rate of a drilling unit can exceed 500 000 USD.

In the process of drilling, mud is essential in order to control the pressure of the well, provide lubrication and cooling, and for transport of drilled out material, often called cuttings. Different muds are needed for different conditions, depending on several factors, resulting in mud of specific properties for specific conditions. The best known parameters characterizing mud are viscosity and density. The mud can be based on water, or mineral or hydrocarbon oil and can include traditional materials like bentonite clays or other natural materials or synthetic materials. The selection and formulation of the mud is managed by the mud engineer.

It is industry practice to monitor the properties of the mud returning from the well. This is essential in order to detect traces of hydrocarbons, particularly traces of gas, which can give an early warning of a gas kick (uncontrolled pressure rise).

However, with respect to the mud to be pumped down into the well by the mud pumps, it is industry practice to take manual samples in order to ensure that the mud properties are as intended. The sample must typically be sent to a laboratory, either on the drilling rig or on land at a remote location, and the process of analyzing may take considerable time. For drilling operations offshore, time is very expensive, and even a moderate reduction in wasted time can have a significant impact on the economy of the operation. Another aspect is the increased safety if it could be ensured at all times that only mud having the correct properties is pumped down the drill string.

Many technologies exist for data acquisition and processing of data. Many technologies exists for collecting samples of mud coming up from the well, and some for collecting samples of mud as mixed and to be pumped down the drill string. In addition, many technologies exist for analyzing single parameters of the mud.

Some related technology is described in the patent publications CN 201802388, GB 2445209, CA 2005195, MX 2011006044 and U.S. Pat. No. 6,378,628.

However, a demand still exists for technology in order to: reduce the time spent for monitoring the mud properties; provide a continuous monitoring; provide data for more parameters than current industry standard practice: reduce the risk of pumping incorrect mud composition; reduce waste, tankage requirement and ineffective drilling unit time and increase safety. The objective of the present invention is to meet the demand.

SUMMARY OF THE INVENTION

The invention meets the demand by providing a system for real time mud monitoring. The system is distinctive in that it comprises
  means for real time continuous or frequent measurement of a diversity of mud parameters of the mud being pumped into the well, said parameters at least comprising mud weight/density and viscosity,
  a skid where the means for measurements are arranged, said means are connected in real time to a mud process for measurements and to a data collection and analysis system connected in real time and interfaced to a mud engineer.

Preferably the means are arranged in a conduit for suction to the mud pumps or a parallel branch line, or connected to mud pits, and preferably also in the mud return flow downstream or upstream or both downstream and upstream of the shale shakers. The system can comprise means arranged upstream of the mud pump, for measuring mud property parameters as delivered and pumped down the well. Instrumentation not requiring batch measurements are preferably arranged in the mud pump suction line. The system is normally installed on the suction line/low pressure side, however, instruments with relevant pressure class can also be installed on the high pressure side. The pressure class of the sensors or instrumentation of the means must be compatible with the mud pressure from the mud pump if installed on the delivery side of said pump.

The real time interface to the mud engineer preferably comprises a display visualizing the measured mud properties. The system is also connected to a database including mud properties and well property data, empirical and theoretical, and the system comprises real time connection to the instrumentation arranged operatively to the mud flow. The system preferably comprises or is coupled to analysis algorithms, for using real time quality data of properties of mud to be pumped down the well and preferably also real time quality data on mud return flow properties, including comparison of pumped in mud properties with returned mud properties, for generating estimates and proposals for future action.

Said means for real time continuous or frequent measurement of a diversity of mud parameters comprises instrumentation for measuring two or more of:
  Temperature −5 to +200° C.
  Mud weight/density 500-3000 g/l
  Oil/water 0-100%
  Viscosity 10-150000 Cp or 10-500000 Cp
  Rheology 10-500000 Cp at 3, 6, 30, 60, 100, 200, 300 and 600 rpm
  Gel strength at 10 seconds, 10 minutes and 30 minutes
  pH 0-14
  hardness/conductivity 5 µS/cm-2000 mS/cm
  solids and liquids breakdown 0-100%
  sand content/particle size analysis 0.7 micron-4.8 mm
  pressure 100 mbar-40 bar
  API fluid loss
  Filter cake
  Calcium and Magnesium content
  Chloride content
  Potassium content
  Alkalinity (lime content)
  MBT (clay content)
  HTHP filter
  Electric stability The instrumentation is preferably of the type certified to operate in gaseous hazardous atmospheres, arranged in an optimized skid, with a certified hazardous atmosphere electrical, optical or wireless connection to a control room or similar having analysis and data storage capacity feasible for the mud engineer, or having real time connection to the mud engineer. Feasible instrumentation is commercially available in the market, from the shelf or on order from producers or suppliers.

The connection in real time to a mud engineer is to a control room located offshore or onshore or a mud engineer located onshore.

The system preferably generates a proposal for action, based on collected and processed data, and the proposal is presented to the mud engineer.

The invention also provides a method for increased control of a drilling process, by using a system of the invention. The method is distinctive by the steps:

to arrange said system for real time continuous or frequent measurement of a diversity of mud parameters of the mud being pumped into the well, said parameters at least comprising mud weight/density and viscosity, to arrange said system to a data collection and analysis system connected and interfaced in real time to a mud engineer, and to measure in real time, continuously or frequently, parameters of the mud being pumped into the well.

The invention also provides use of the system of the invention, for real time mud monitoring of the mud being pumped into the well.

FIGURES

FIG. 1 illustrates an embodiment a system of the invention.

DETAILED DESCRIPTION

Reference is made to FIG. 1, illustrating a system for real time mud monitoring, comprising means, which is instrumentation, for real time continuous or frequent measurement of a diversity of mud parameters. Said means, in the illustrated embodiment and in the direction of flow of mud, comprises a thermometer, a conductivity meter, a density meter and a pH meter, connected in series; an oil/water/solids particle size analyzer and a viscosity meter coupled in series but with a rheometer coupled in parallel; and a pressure meter. Said means or instrumentation are connected in real time to the mud process for measurements, which can be seen by the mud in and mud out flow direction, as indicated on the FIGURE. Not illustrated specifically on the FIGURE, said instruments are also connected in real time to a data collection and analysis system connected in real time and interfaced to a mud engineer.

The mud engineer, which is the term used for the person or team managing the mud system, will accordingly have status of essential and not so essential mud parameters, their history and analysis tools for calculating adjustments to the mud formulation. The coupling from the instrumentation to the mud engineer, is by cable, fibre or via wireless communication. If the mud engineer is stationed remotely, the connection to the remote location is preferably by optical fibers.

As a minimum, the system comprises instrumentation of the always essential parameters mud weight/density and viscosity, but preferably also pressure, rheology, oil contents, gel strength and temperature.

Measuring the properties of the mud to be pumped into the well in real time for a variety of parameters, the measurements being coupled in real time to the mud engineer, is novel as far as the applicant know. Measuring the properties of the mud returning from the well, preferably identical parameters as for the mud to be pumped into the well, the measurements being coupled in real time to the mud engineer, is novel as far as the applicant know. Comparing said measurements with respect to properties and over time, which is a preferable embodiment of the invention, provides an additional means for control of the drilling process, resulting in higher efficiency and improved safety.

Some further advantages of the present invention are as follows:

1. interface otherwise known technology into the existing mud process. The skid mounted system of the invention can easily be retrofitted to existing mud systems or installed in new mud systems.
2. Gain mud properties automatically from the mud process. Reduce time and uncertainty by using a standardized automated system with continuous measurements, which is not available to the industry today.
3. Deliver real time mud properties data from one unit from the mud system overall or for specific data, directly to a user (software or person) from the installed set of instruments and processing software.

Some Skid Key Features:

Measurement skid, (some instrument can be located remotely/outside skid), allowing continues flow of mud through the skid.

Allow variable flow of mud through the skid to optimize measurements

Allow automated batch measurements in parallel to the continuous flow allowing measurements in "still standing fluid"

Generation of mud reports and trends of parameters provided to a given software interface, or directly displayed on the skid Combination of measurements taken by one "unit"

Ex certified

Fit to existing installations, can be installed off line main process

Batch measuring for feasible parameters like gel and rheology parameters, is one of or key benefits. The mud is routed through the skid/a loop and then provide each instrument with optimal conditions for measuring, giving better and more precise readings. Reduced data treatment afterwards.

No other technology than the technology of the invention can ensure the drilling fluid or mud being pumped down into the well has correct composition, with correct properties, and no other technology can achieve such result so fast, simple and consistently. Moreover, no other technology is so feasible for retrofitting into existing drilling fluid systems, without large modifications.

The system of the invention may comprise any feature or step as here described or illustrated, in any operative combination, and each such combination is an embodiment of the present invention. The method of the invention may comprise any feature or step as here described or illustrated, in any operative combination, and each such combination is an embodiment of the present invention. The use of the invention may comprise any feature or step as here described or illustrated, in any operative combination, and each such combination is an embodiment of the present invention.

The invention claimed is:

1. A system for real time mud monitoring, the system comprising:
   a density meter measuring mud weight/density in a range of 500-3000 g/l and a viscosity meter measuring viscosity in a range of 10-150000 Cp or 10-500000 CPi;
   a rheometer that measures rheology 10-500000 Cp at a plurality of specific flow rates;
   wherein each of the plurality of specific flow rates is related to a specific pump rpm;
   wherein the density meter and the viscosity meter are coupled inline in a mud flow line under high pressure on a delivery side of a mud pump and are arranged for measuring continuously in real time in mud under high pressure being pumped into a well;
   a skid where the density meter and the viscosity meter are arranged; and
   wherein the density meter and the viscosity meter are connected in real time to a data collection and analysis system interface for delivering collected data and analysis to a mud engineer.

2. The system according to claim 1, wherein the density meter and the viscosity meter are two of several further meters being part of instrumentation coupled inline in at least one mud flow lines and being arranged in the skid.

3. The system according to claim 1, wherein the system comprises analysis algorithms, for using real time quality data of properties of mud to be pumped down the well, and also real time quality data on mud return flow properties, including comparison of pumped in mud properties with returned mud properties, for generating estimates and proposals for future action.

4. The system according to claim 2, wherein the further instrumentation comprises at least one of:
   Temperature −5 to +200° C.;
   Oil/water 0-100%;
   Rheology 10-500000 Cp at 3, 6, 30, 60, 100, 200, 300 and 600 rpm;
   Gel strength at 10 seconds, 10 minutes and 30 minutes;
   pH 0-14;
   hardness/conductivity 5 μS/cm-2000 mS/cm;
   solids and liquids breakdown 0-100%;
   sand content/particle size analysis 0.7 micron-4.8 mm;
   pressure 100 mbar- to full pressure pumping into the well;
   API fluid loss;
   Filter cake;
   Calcium and Magnesium content;
   Chloride content;
   Potassium content;
   Alkalinity (lime content);
   MBT (clay content);
   HTHP filter; and
   Electric stability.

5. The system according to claim 1, wherein the density meter and the viscosity meter are configured to operate in gaseous hazardous atmospheres, arranged in the skid, with a connection to a control room having analysis and data storage capacity feasible for the mud engineer.

6. The system according to claim 1, wherein the interface in real time to the mud engineer is to a control room located at least one of offshore or onshore.

7. The system according to claim 1, wherein a proposal for action is generated by the system, based on collected and processed data, and the proposal is presented to the mud engineer.

8. A method for increased control of a drilling process, by using the system of claim 1, the method comprising:
   arranging said system, including the density meter and the viscosity meter, for real time continuous measurement of at least mud weight/density and viscosity;
   arranging said system to a data collection and analysis system connected and interfaced continuously in real time for delivering collected data and analysis to a mud engineer;
   measuring rheology 10-500000 Cp with a rheometer, at a plurality of specific flow rates controllable by adjusting pump rpm;
   wherein each of the plurality of specific flow rates is related to a specific pump rpm;
   measuring in real time and continuously, parameters of the mud under pressure being pumped into the well; and
   comparing pumped-in mud properties with returned-mud properties for generating estimates and proposals for future actions.

* * * * *